(12) United States Patent
Maitland et al.

(10) Patent No.: US 8,153,421 B2
(45) Date of Patent: Apr. 10, 2012

(54) PROSTATE STEM CELL

(75) Inventors: Norman James Maitland, Claxton (GB); Anne Collins, York (GB)

(73) Assignee: Procure Therapeutics Limited, York (GB)

( * ) Notice: Subject to any disclaimer, the term of this patent is extended or adjusted under 35 U.S.C. 154(b) by 898 days.

(21) Appl. No.: 10/593,128

(22) PCT Filed: Mar. 18, 2005

(86) PCT No.: PCT/GB2005/001142
§ 371 (c)(1),
(2), (4) Date: Jun. 3, 2008

(87) PCT Pub. No.: WO2005/089043
PCT Pub. Date: Sep. 29, 2005

(65) Prior Publication Data
US 2008/0233640 A1 Sep. 25, 2008

(30) Foreign Application Priority Data
Mar. 19, 2004 (GB) .................................. 0406215.4

(51) Int. Cl.
*C12N 5/095* (2010.01)
*C12N 5/00* (2006.01)
(52) U.S. Cl. ....................................... 435/325; 435/402

(58) Field of Classification Search ................. 435/325, 435/402
See application file for complete search history.

(56) References Cited

U.S. PATENT DOCUMENTS
2007/0134794 A1 * 6/2007 Mangano ...................... 435/325

OTHER PUBLICATIONS

Collins et al. (2001), J. Cell Science, vol. 114, 3865-3872.*
Richardson et al. (2004) J. Cell Sci., vol. 117, 3539-3545.*
Bhatt et al., "Novel Method for the Isolation and Characterisation of the Putative Prostatic Stem Cell," *Cytometry Part A* 54A:89-99 (2003).
Collins et al., "Identification and isolation of human prostate epithelial stem cells based on $\alpha_2\beta_1$-integrin," *J. Cell Science* 114:3865-3872 (2001).
Richardson et al., "CD133, a novel marker for human prostatic epithelial stem cells," *J. Cell Science* 117:3539-3545 (2004).
Yin et al., "A C133, a Novel Marker for Human Hematopoietic Stem and Progenitor Cells," *Blood* 90(12):5002-5012 (1997).

* cited by examiner

*Primary Examiner* — Anne Marie S Wehbe
(74) *Attorney, Agent, or Firm* — Crowell & Moring LLP

(57) ABSTRACT

We describe a method for the isolation of prostate stem cells, typically prostate stem cells which express CD 133 antigen; stem cells and cancer stem cells isolated by the method and their use.

10 Claims, 4 Drawing Sheets

Vimentin

Cytokeratin 18

E-Cadherin

PSA

Figure 3

MHRTTRIKITELNPHLMCVLCGGYFIDATTIIECLHSFCKTCIV
RYLETSKYCPICDVQVHKTRPLLNIRSDKTLQDIVYKLVPGLFKNEMKRRRDFYAAHP
SADAANGSNEDRGEVADEDKRIITDDEIISLSIEFFDQNRLDRKVNKDKEKSKEEVND
KRYLRCPAAMTVMHLRKFLRSKMDIPNTFQIDVMYEEEPLKDYYTLMDIAYIYTWRRN
GPLPLKYRVRPTCKRMKISHQRDGLTNAGELESDSGSDKANSPAGGIPSTSSCLPSPSTPVQ
SPHPQFPHISSTMNGTSNSPSGNHQSSFANRPRKSSVNGSSATSSG

Figure 4

```
   1 CAGCAACTAT GAAATAATCG TAGTATGAGA GGCAGAGATC GGGGCGAGAC AATGGGGATG
  61 TGGGCGCGGG AGCCCCGTTC CGGCTTAGCA GCACCTCCCA GCCCCGCAGA ATAAAACCGA
 121 TCGCGCCCCC TCCGCGCGCG CCCTCCCCCG AGTGCGGAGC GGGAGGAGGC GGCGGCGGCC
 181 GAGGAGGAGG AGGAGGAGGC CCCGGAGGAG GAGGCGTTGG AGGTCGAGGC GGAGGCGGAG
 241 GAGGAGGAGG CCGAGGCGCC GGAGGAGGCC GAGGCGCCGG AGCAGGAGGA GGCCGGCCGG
 301 AGGCGGCATG AGACGAGCGT GGCGGCCGCG GCTGCTCGGG GCCGCGCTGG TTGCCCATTG
 361 ACAGCGGCGT CTGCAGCTCG CTTCAAGATG GCCGCTTGGC TCGCATTCAT TTTCTGCTGA
 421 ACGACTTTTA ACTTTCATTG TCTTTTCCGC CCGCTTCGAT CGCCTCGCGC CGGCTGCTCT
 481 TTCCGGGATT TTTTATCAAG CAGAAATGCA TCGAACAACG AGAATCAAGA TCACTGAGCT
 541 AAATCCCCAC CTGATGTGTG TGCTTTGTGG AGGGTACTTC ATTGATGCCA CAACCATAAT
 601 AGAATGTCTA CATTCCTTCT GTAAACGTG TATTGTTCGT TACCTGGAGA CCAGCAAGTA
 661 TTGTCCTATT TGTGATGTCC AAGTTCACAA GACCAGACCA CTACTAATA TAAGGTCAGA
 721 TAAAACTCTC CAAGATATTG TATACAAATT AGTTCCAGGG CTTTTCAAAA ATGAAATGAA
 781 GAGAAGAAGG GATTTTTATG CAGCTCATCC TTCTGCTGAT GCTGCCAATG GCTCTAATGA
 841 AGATAGAGGA GAGGTTGCAG ATGAAGATAA GAGAATTATA ACTGATGATG AGATAATAAG
 901 CTTATCCATT GAATTCTTTG ACCAGAACAG ATTGGATCGG AAAGTAAACA AAGACAAAGA
 961 GAAATCTAAG GAGGAGGTGA ATGATAAAAG ATACTTACGA TGCCCAGCAG CAATGACTGT
1021 GATGCACTTA AGAAAGTTTC TCAGAAGTAA AATGGACATA CCTAATACTT TCCAGATTGA
1081 TGTCATGTAT GAGGAGGAAC CTTTAAAGGA TTATTATACA CTAATGGATA TTGCCTACAT
1141 TTATACCTGG AGAAGGAATG GTCCACTTCC ATTGAAATAC AGAGTTCGAC CTACTTGTAA
1201 AAGAATGAAG ATCAGTCACC AGAGAGATGG ACTGACAAAT GCTGGAGAAC TGGAAAGTGA
1261 CTCTGGGAGT GACAAGGCCA ACAGCCCAGC AGGAGGTATT CCCTCCACCT CTTCTTGTTT
1321 GCCTAGCCCC AGTACTCCAG TGCAGTCTCC TCATCCACAG TTTCCTCACA TTTCCAGTAC
1381 TATGAATGGA ACCAGCAACA GCCCCAGCGG TAACCACCAA TCTTCTTTTG CCAATAGACC
1441 TCGAAAATCA TCAGTAAATG GGTCATCAGC AACTTCTTCT GGTTGATACC TGAGACTGTT
1501 AAGGAAAAAA ATTTTAAACC CCTGATTTAT ATAGATATCT TCATGCCATT ACAGCTTTCT
1561 AGATGCTAAT ACATGTGACT ATCGTCCAAT TTGCTTTCTT TTGTAGTGAC ATTAAATTTG
1621 GCTATAAAAG ATGGACTACA TGTGATACTC CTATGGACGT TAATTGAAAA GAAAGATTGT
1681 TGTTATAAAG AATTGGTTTC TTGGAAAGCA GGCAAGACTT TTTCTCTGTG TTAGGAAAGA
1741 TGGGAAATGG TTTCTGTAAC CATTGTTTGG ATTTGGAAGT ACTCTGCAGT GGACATAAGC
1801 ATTGGGCCAT AGTTTGTTAA TCTCAACTAA CGCCTACATT ACATTCTCCT TGATCGTTCT
1861 TGTTATTACG CTGTTTTGTG AACCTGTAGA AAACAAGTGC TTTTTATCTT GAAATTCAAC
1921 CAACGGAAAG AATATGCATA GAATAATGCA TTCTATGTAG CCATGTCACT GTGAATAACG
1981 ATTTCTTGCA TATTTAGCCA TTTTGATTCC TGTTTGATTT ATACTTCTCT GTTGCTACGC
2041 AAAACCGATC AAAGAAAAGT GAACTTCAGT TTTACAATCT GTATGCCTAA AAGCGGGTAC
2101 TACCGTTTAT TTTACTGACT TGTTTAAATG ATTCGCTTTT GTAAGAATCA GATGGCATTA
2161 TGCTTGTTGT ACAATGCCAT ATTGGTATAT GACATAACAG GAAACAGTAT TGTATGATAT
2221 ATTTATAAAT GCTATAAGA AATATTGTGT TCATGCATT CAGAAATGAT TGTTAAAATT
2281 CTCCCAACTG GTTCGACCTT TGCAGATACC CATAACCTAT GTTGAGCCTT GCTTACCAGC
2341 AAAGAATATT TTTAATGTGG ATATCTAATT CTAAAGTCTG TTCCATTAGA AGCAATTGGC
2401 ACATCTTTCT ATACTTTATA TACTTTTCTC CAGTAATACA TGTTTACTTT AAAAATTGTT
2461 GCAGTGAAGA AAAACCTTTA ACTGAGAAAT ATGGAAACCG TCTTAATTTT CCATTGGCTA
2521 TGATGGAATT AATATTGTAT TTTAAAAATG CATATTGATC ACTATAATTC TAAAACAATT
2581 TTTTAAATAA ACCAGCAGGT TGCTAAAAGA AGGCATTTTA TCTAAAGTTA TTTTAATAGG
2641 TGGTATAGCA GTAATTTTAA ATTTAAGAGT TGCTTTTACA GTTAACAATG GAATATGCCT
2701 TCTCTGCTAT GTCTGAAAAT AGAAGCTATT TATTATGAGC TTCTACAGGT ATTTTTAAAT
2761 AGAGCAAGCA TGTTGAATTT AAAATATGAA TAACCCACC CAACAATTTT CAGTTTATTT
2821 TTTGCTTTGG TCGAACTTGG TGTGTGTTCA TCACCCATCA GTTATTTGTG AGGGTGTTTA
2881 TTCTATATGA ATATTGTTTC ATGTTTGTAT GGGAAAATTG TAGCTAAACA TTTCATTGTC
2941 CCCAGTCTGC AAAAGAAGCA CAATTCTATT GCTTTGTCTT GCTTATAGTC ATTAAATCAT
3001 TACTTTTACA TATATTGCTG TTACTTCTGC TTTCTTTAAA AATATAGTAA AGGATGTTTT
3061 ATGAAGTCAC AAGATACATA TATTTTTATT TTGACCTAAA TTTGTACAGT CCCATTGTAA
3121 GTGTTGTTTC TAATTATAGA TGTAAAATGA AATTTCATTT GTAATTGGAA AAAATCCAAT
3181 AAAAGGATA TTCATTTAGA AAAAAAAAAA AAAAAAAAAA AAAAAAAAAA AAAAAAAAAA
3241 AAAAAAAAAA A
```

PROSTATE STEM CELL

CROSS REFERENCE TO RELATED APPLICATIONS

This is a §371 U.S. national stage of PCT/GB2005/001142, filed Mar. 18, 2005, which was published in English under PCT Article 2(2), and claims the benefit of Great Britain application 0406215.4, filed Mar. 19, 2004. Both applications are incorporated herein in their entirety.

The invention relates to a method for the isolation of prostate stem cells, typically prostate cancer stem cells; stem cells and cancer stem cells isolated by the method and their use.

The prostate gland is the major accessory organ of the male reproductive tract, and is the most common site of neoplastic disorders in men. The two main pathologies of the gland are: (i) benign prostatic hyperplasia, which is a non-malignant condition that is common with age and (ii) carcinoma, which is the second most common cause of death in European men, after lung cancer and is increasingly prevalent in our ageing Western Society. Symptoms include, blood in the semen or the urine, frequent pain or stiffness in the lower back, hips or upper thigh. Prostate tumours may be primary (i.e. located in the organ of origin) or secondary (i.e. tumours which form in other organs due to the ability of cancerous cells to move and invade other tissues via the circulatory system).

Prostate cancer can be relatively harmless or extremely aggressive. Some prostate tumours are slow growing and cause few clinical symptoms. Aggressive prostate tumours spread rapidly to the lymph nodes and other organs, especially bone. It is known that the growth of prostate cancer can be inhibited by blocking the supply of male hormones such as testosterone. However, prostate cancers eventually develop and become independent of male sex hormones (i.e. they become androgen-independent prostate cancer cells). These cells are linked with aggressive, malignant prostate cancer. All male mammals have a prostate gland but only humans and dogs are known to naturally develop prostate cancer.

Metastatic prostate cancers predominantly move to the bone and are treated by reducing the production of androgens by blocking androgen production by the adrenal glands and testis. This treatment is only effective for a short period of time as the metastatic lesions become androgen independent and grow uncontrollably.

The presence of androgen independent prostate cancer cells means that this treatment regime is no longer effective and further intervention is required to control the progress of the disease. A similar response is seen to chemotherapeutic and radiotherapy treatments. As a result, metastatic prostate cancer remains an incurable disease by current treatment strategies. There is therefore a continual need to identify new therapeutic targets to provide new treatments for prostate cancer.

A problem underlying the effective treatment of cancerous conditions is the identification of a population of cells in a tumour that have the ability of sustaining the growth of a tumour. The evidence suggests that tumours are clonal and are therefore derived from a single cell. However, there are few studies that identify and characterise those cells types that are responsible for maintaining tumour cell growth. Some have searched for these so called "cancer stem cells".

WO03/050502 discloses a method to selectively enrich breast tumour stem cells through the use of a xenograft model in which human breast cancer cells were grown in immuno-compromised mice. WO03/102215 describes the isolation of stem cells and cancer stem cells by virtue of the specific expression of a reporter gene that is regulated by β catenin that becomes actively expressed in a stem cell. US2003119080 describes a method for the isolation of tumour stem cells from solid tumours. In WO0140309 is a described antibody to an alleged prostate stem cell antigen, referred to as prostate stem cell antigen (PSCA) which is also described in U.S. Pat. No. 5,856,136, WO99/14328 and WO98/51805.

We have identified CD133, which is expressed by primitive haematopoietic stem cells and developing epithelia as a further stem cell marker for prostate epithelia. CD133 cells are restricted to the $\alpha_2\beta_1^{hi}$ population (the receptor for type I collagen) and are located in the basal layer, often at the base of a budding region or branching point (FIG. 1A). $\alpha_2\beta_1^{hi}$/CD133$^+$ cells exhibit two important attributes of epithelial stem cells: they possess a high in vitro proliferative potential (FIG. 1B) and can reconstitute prostatic-like acini in immunocompromised male nude mice FIG. 1C). can reconstitute prostatic-like acini in immunocompromised male nude mice FIG. 1C).

Prostate tumour stem cells have been directly isolated from lymph node and prostate glands from a series of patient samples using the following markers: human epithelial antigen (HEA), CD44 (which is expressed by basal cells in the prostate; Liu et al., 1997), $\alpha_2\beta_1^{hi}$ and CD133. Morphologically the cells range from fibroblastoid (expressing high levels of vimentin which is typical of transformed cells) or epithelial, and are capable of producing progenitors associated with prostate epithelial differentiation (FIG. 2A). Invasion assays, using Matrigel-coated filters have determined that these cells have a similar capacity to invade through Matrigel than PC3M (a highly metastatic subline of PC3 cells (FIG. 2B).

We describe a method to selectively enrich for prostate stem cells or prostate cancer stem cells that utilises the differential adhesion to type I collagen and growth of stem cells in culture to select a population of cells with prostate stem cell potential.

According to an aspect of the invention there is provided a method for the isolation of prostate stem cells comprising the selective enrichment of prostate cells which express CD133 antigen. Preferably said stem cells also express high levels of $\alpha_2\beta_1$ integrin.

In a preferred method of the invention said selective enrichment comprises the following steps:
i) providing a cell preparation comprising prostate cells derived from prostate tissue;
ii) providing cell culture conditions which allow the maintenance of said prostate cells in culture and the binding of said prostate cells to a collagen matrix;
iii) selecting said bound cells wherein said cells express CD133 antigen.

In a preferred method of the invention said method includes the additional steps of:
i) culturing cells which express CD133 antigen in culture medium comprising; granulocyte macrophage colony stimulating factor (GM-CSF), stem cell factor (SCF) and leukaemia inhibitory factor (LIF); and
ii) passaging the selected cells in (i) in a serum free medium.

In an alternative method of the invention said matrix is a non-collagen based peptide matrix. An example of such a non-collagen based peptide matrix is PuraMatrix™.

In a further preferred method of the invention said selected cells express epithelial antigen, preferably human epithelial antigen.

In a yet further preferred method of the invention said selected cells express CD44 antigen.

In a still further preferred method of the invention said selected cells do not express telomerase.

In a preferred method of the invention said prostate derived tissue comprises cancerous prostate cells.

In a further preferred method of the invention said cancerous prostate cells are derived from malignant prostate derived tissue.

In a preferred method of the invention said cancerous prostate cells are derived from primary or metastatic lymph node sites.

In a further preferred method of the invention said collagen based matrix comprises collagen I.

According to a further aspect of the invention there is provided a prostate stem cell obtainable by the method according to the invention.

In a preferred embodiment of the invention said cell is a prostate cancer stem cell.

In a further preferred embodiment of the invention said stem cell is a cloned cell.

According to a further aspect of the invention there is provided a substantially pure culture of prostate stem cells wherein said cells express CD133 antigen. Preferably said cells are prostate cancer stem cells.

In a preferred embodiment of the invention said cells express high levels of $\alpha_2\beta_1$ integrin.

In a further preferred embodiment of the invention said cells express human epithelial antigen. Preferably said cells express CD44 antigen.

In a yet further preferred embodiment of the invention said cells express CD133 antigen, high levels of $\alpha_2\beta_1$ integrin, human epithelial antigen and CD44 antigen.

Prostate stem cells/prostate cancer stem cells are typically characterised by specific phenotypic characteristics. For example, cells with stem cell potential are able to divide in culture in an undifferentiated state for multiple passages; able to form all the cell-types found in prostate tissue; and express gene markers of prostate stem cells and/or differentiated prostate cells. These characteristics are merely meant to be illustrative of prostate stem cells and not meant to be restrictive.

According to a further aspect of the invention there is provided a prostate stem cell preparation obtainable by the method according to the invention for use as in a vaccine composition.

It will be apparent that the prostate stem cells selected by the method according to the invention have utility with respect to the selection of genes expressed in normal prostate stem cells and also cancerous prostate stem cells. Antibodies generated to these expressed sequences are useful since they represent potential targets for the development of vaccines which may be used prophylatically or therapeutically to treat those with a predisposition to prostate cancer or are suffering from either primary prostate cancer or from secondary prostate cancer as a result of metastasis from a primary cancer. Antibodies generated will also have utility with respect to the diagnosis of prostate cancer.

In a preferred embodiment of the invention said prostate stem cell is a cancerous prostate stem cell.

According to a further aspect of the invention there is provided a vaccine composition comprising a prostate stem cell according to the invention.

In a preferred embodiment of the invention said composition includes an adjuvant and/or a carrier.

An adjuvant is a substance or procedure that augments specific immune responses to antigens by modulating the activity of immune cells. Examples of adjuvants include, by example only, Freunds adjuvant, muramyl dipeptides, liposomes. A carrier is an immunogenic molecule which, when bound to a second molecule, augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen. Helper T-cells can also stimulate other immune cells such as cytotoxic T-cells, and a carrier can fulfil an analogous role in generating cell-mediated immunity as well as antibodies.

According to a further aspect of the invention there is provided a method to immunise an animal comprising administering an effective amount of a prostate stem cell preparation according to the invention.

In a preferred method of the invention said cell preparation comprises cancerous prostate stem cells according to the invention.

In a preferred method of the invention said animal is a human.

In an alternative preferred method of the invention said animal is a rodent, preferably a rat, mouse of hamster.

In a further preferred method of the invention said animal is a rabbit, goat or sheep.

In a yet further preferred method of the invention said animal is a dog.

A preferred route of administration is intradermal, subcutaneous, intramuscular, oral or intranasal; however the immunisation method is not restricted to a particular mode of administration.

According to a further aspect of the invention there is provided an antibody obtainable by the method according to the invention.

In a preferred embodiment of the invention said antibody is a therapeutic antibody.

In a further preferred embodiment of the invention said antibody is a diagnostic antibody. Preferably said diagnostic antibody is provided with a label or tag.

In a preferred embodiment of the invention said antibody is a monoclonal antibody or binding fragment thereof. Preferably said antibody is a humanised or chimeric antibody.

A chimeric antibody is produced by recombinant methods to contain the variable region of an antibody with an invariant or constant region of a human antibody.

A humanised antibody is produced by recombinant methods to combine the complementarity determining regions (CDRs) of an antibody with both the constant (C) regions and the framework regions from the variable (V) regions of a human antibody. Chimeric antibodies are recombinant antibodies in which all of the V-regions of a mouse or rat antibody are combined with human antibody C-regions. Humanised antibodies are recombinant hybrid antibodies that fuse the complimentarily determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

It is also possible to create single variable regions, so called single chain antibody variable region fragments (scFvs). If a hybridoma exists for a specific monoclonal antibody it is well within the knowledge of the skilled person to isolate scFvs from mRNA extracted from said hybridoma via RT PCR. Alternatively, phage display screening can be undertaken to identify clones expressing scFvs. Alternatively said fragments are "domain antibody fragments". Domain antibodies are the smallest binding part of an antibody (approximately 13 kDa). Examples of this technology is disclosed in U.S. Pat. Nos. 6,248,516, 6,291,158, 6,127,197 and EP0368684 which are all incorporated by reference in their entirety.

In a further preferred embodiment of the invention said antibodies are opsonic antibodies.

Phagocytosis is mediated by macrophages and polymorphic leukocytes and involves the ingestion and digestion of micro-organisms, damaged or dead cells, cell debris, insoluble particles and activated clotting factors. Opsonins are agents that facilitate the phagocytosis of the above foreign bodies. Opsonic antibodies are therefore antibodies which provide the same function. Examples of opsonins are the Fc portion of an antibody or compliment C3. Antibodies raised by immunisation and in the form of an immune complex with antigen may bring about opsonisation via the fixation of complement on the antigen, or molecules in its immediate microenvironment.

According to a further aspect of the invention there is provided an antibody according to the invention for use as a pharmaceutical.

According to a further aspect of the invention there is provided a pharmaceutical composition comprising an antibody according to the invention.

According to a further aspect of the invention there is provided a T-lymphocyte obtainable by the method according to the invention.

Preferably said T-lymphocytes are T-helper lymphocytes.

The immune system is made up in part of lymphocytes which are able to recognise specific antigens. B lymphocytes recognise antigens in their native conformation through surface immunoglobulin receptors, and T lymphocytes recognise protein antigens that are presented as peptides along with self molecules known as major histocompatibility antigen (MHC), or human leukocyte antigen (HLA) in humans, on the surface of antigen presenting cells. Antigen presenting cells occur in different forms and may be distinguished into 'classical' antigen presenting cells, exemplified by macrophages and dendritic cells and 'non-classical' antigen presenting cells, which includes B lymphocytes. T lymphocytes may be further subdivided into "cytotoxic T lymphocytes", which are able to kill, for example virally infected target cells, and "T helper" lymphocytes. T helper lymphocytes have a regulatory function and are able to "help" B lymphocytes to produce specific antibody, or to help macrophages to kill cancer cells.

According to a further aspect of the invention there is provided a method for the identification of genes associated with prostate stem cells comprising the steps of:

i) providing a preparation comprising at least one prostate stem cell according to the invention;
ii) extracting nucleic acid from said cell preparation;
iii) contacting said extracted nucleic acid with a nucleic acid array; and
iv) detecting a signal which indicates the binding of said nucleic acid to a binding partner on said nucleic acid array. Preferably said method includes the additional steps of:
i) collating the signal(s) generated by the binding of said nucleic acid to said binding partner;
ii) converting the collated signal(s) into a data analysable form; and optionally;
iii) providing an output for the analysed data.

In a preferred method of the invention said preparation comprises cancer prostate stem cells.

In a further preferred method of the invention said method includes a comparison of the array signal produced between normal and cancer prostate stem cells.

In an alternative preferred method of the invention said method includes a comparison of the array signal produced between a first cancer prostate stem cell sample and a second, different cancer prostate stem cell sample.

According to a further aspect of the invention there is provided a method for the preparation of a library comprising prostate specific gene expression products comprising the steps:

i) providing a preparation comprising at least one prostate stem cell according to the invention;
ii) extracting nucleic acid from said cell preparation;
iii) preparing a cDNA from ribonucleic acid contained in said extracted nucleic acid; and
iv) ligating cDNA formed in (iii) into a vector.

In a preferred method of the invention said vector is a phage based vector.

In our PCT application, WO03/014334 we have developed an in vitro cell culture method which provides a culture regime that allows prostate epithelial cells to form prostate-like-acini which closely resemble prostate acini found in vivo. The method relies on a combination of serum, hormones and a suitable cell matrix support which allows the epithelial cells to attach, proliferate, differentiate and form prostatic-like-acini. The system is able to support growth of cloned normal prostate epithelial cells as well as cloned cancerous prostate cells, primary prostate epithelial cells and primary cancerous prostate cells to provide a 3D structure which reflects the in vivo state. The system is invaluable for the study of prostate cell differentiation and prostate cell transformation. It will provide a tool for use in the identification of agents effective at inhibiting the proliferation and metastasis of prostate cancer cells and also to identify novel markers of prostate cell differentiation and transformation. We disclose herein that prostate stem cells selected by the method according to the invention are able to form prostate-like acini as described in WO03/014334, which is incorporated by reference in its entirety and more specifically the culture conditions for the formation of prostate-like acini.

According to an aspect of the invention, there is provided an in vitro method for the formation of prostate-like acini comprising:

i) providing a cell culture vessel comprising:
a) prostate stem cells according to the invention;
b) a cell culture support matrix to which the cells in (a) can attach and proliferate;
c) cell culture medium supplemented with serum, a stromal fraction and a ratio of the hormones oestrogen and dihydrotestosterone, or functional derivatives thereof; and ii) providing conditions which promote the growth and differentiation of said prostate derived cells in said vessel.

In a preferred method of the invention the serum is provided at between about 0.5%-4% (v/v). Preferably said serum is provided at about between 1%-3% (v/v). Most preferably said serum is provided at about 2% (v/v).

In a further preferred method of the invention oestrogen is provided at about 10 ng/ml and dihydrotestosterone at about $10^{-7}$ M.

According to a further aspect of the invention there is provided an in vitro method for the formation of vascularised prostate acini comprising the steps of:
i) providing a cell culture vessel which includes: prostate-like acini formed from prostate stem cells according to the invention that have been formed in a cell culture medium supplemented with serum, a stromal fraction, and a ratio of oestrogen and dihydrotestosterone, or functional derivatives thereof, a cell culture support matrix; and a cell culture medium which supports the growth of said prostate acini; and
ii) addition of endothelial cells, preferably activated endothelial cells, to said cell culture vessel wherein said endothelial cells proliferate and/or migrate to form blood vessel tubules in or around said prostate acini.

According to an aspect of the invention, there is provided an in vitro method for the formation of vascularised prostate-like acini comprising:
i) providing a cell culture vessel which includes:
a) prostate stem cells and activated endothelial cells;
b) a cell culture support matrix to which the cells in (a) can attach and proliferate;
c) cell culture medium supplemented with serum, a stromal fraction and a ratio of the hormones oestrogen and dihydrotestosterone, or functional derivatives thereof; and
ii) providing conditions which promote the growth and differentiation of said prostate stem cells in said vessel to form prostate acini and the vascularisation of said acini by the formation of blood vessel tubules from said activated endothelial cells.

In a preferred method of the invention said prostate epithelial cells and endothelial cells are of human origin.

"Vessel" is defined as any means suitable to contain the above described cell culture. Typically, examples of such a vessel is a petri dish; cell culture bottle or flask; multiwell culture dishes.

According to a further aspect of the invention there is provided a prostate-like acinus obtainable by the method according to the invention.

In a preferred embodiment of the invention said prostate-like acinus comprises genetically engineered prostate cells.

Genetic engineering may be undertaken to introduce a gene or genes into a stem cell from which an acinus can then be formed. For example, and not by way of limitation, pro-drug activating genes may be transfected into prostatic cells to monitor the efficacy of pro-drugs as cytotoxic agents. A pro-drug activating gene refers to a gene the expression of which results in the production of protein capable of converting a non-therapeutic compound into a therapeutic compound, which renders the cell susceptible to killing by external factors or causes a toxic condition in the cell.

An example of a prodrug activating gene is the cytosine deaminase gene. Cytosine deaminase converts 5-fluorocytosine to 5-fluorouracil, a potent antitumor agent. The lysis of the tumor cell provides a localized burst of cytosine deaminase capable of converting 5FC to 5FU at the localized point of the tumour resulting in the killing of many surrounding tumour cells. This results in the killing of a large number of tumour cells without the necessity of infecting these cells with a vector (the so-called "bystander effect"). Another example of a prodrug-activating gene is thymidine kinase (TK) (see U.S. Pat. Nos. 5,631,236 and 5,601,818) in which the cells expressing the TK gene product are susceptible to selective killing by the administration of gancyclovir. This is merely meant to be illustrative of recombinant methods which could be used in combination with the cells according to the invention. Other examples may include the transfection of tumour suppressor genes, (e.g. p53). The term tumour suppressor gene refers to a nucleotide sequence, the expression of which in a target cell is capable of suppressing the cancerous phenotype and/or inducing apoptosis.

According to a further aspect of the invention there is provided a method to identify agents capable of inhibiting the proliferation of cancerous prostatic cells comprising:
i) providing culture conditions and at least one cancerous acinus according to the invention;
ii) adding at least one agent to be tested; and
iii) monitoring the anti-proliferative activity of the agent with respect to the cells comprising the cancerous acinus.

According to a yet further aspect of the invention there is provided a method to identify agents capable of inhibiting the motility of cancerous prostatic cells comprising:
i) providing culture conditions and at least one cancerous acinus according to the invention;
ii) adding at least one agent to be tested; and
iii) monitoring the motility of cells comprising the cancerous acinus.

According to a further aspect of the invention there is provided a method to identify markers of prostate cell differentiation comprising the steps:
i) providing a preparation comprising prostate stem cells according to the invention; and
ii) determining the expression of at least one gene the expression of which is associated with the differentiation of prostate cells.

According to a further aspect of the invention there is provided a method to identify markers of prostate cell transformation comprising the steps of:
i) providing a preparation comprising prostate stem cells according to the invention; and
ii) determining the expression of at least one gene the expression of which is associated with the transformation of prostate cells.

Methods used in the identification of cell differentiation markers and/or markers of prostate cell transformation include immunogenic based techniques (eg using the cells as complex immunogens to develop antisera to cell surface markers as described above and the like) nucleic acid based techniques (e.g. differential screening using cDNA from normal and transformed acini). Also, it has been known for many years that tumour cells produce a number of tumour cell specific antigens, some of which are presented at the tumour cell surface. These are generally referred to as tumour rejection antigens and are derived from larger polypeptides referred to as tumour rejection antigen precursors. Tumour rejection antigens are presented via HLA's to the immune system. The immune system recognises these molecules as foreign and naturally selects and destroys cells expressing these antigens. If a transformed cell escapes detection and becomes established a tumour develops. Vaccines have been developed based on dominant tumour rejection antigens to provide individuals with a preformed defence to the establishment of a tumour. The method according to the invention provides a means to identify tumour rejection antigens and precursors which will have utility with respect to vaccine development to provoke the patients own immune system to deter the establishment of prostate tumours.

In a preferred method of the invention said gene is an oncogene.

Preferably said oncogene is encoded by a nucleic acid molecule comprising a nucleic acid sequence as represented in FIG. 3, or a nucleic acid molecule that hybridises to said nucleic acid under stringent hybridisation conditions and which encodes a polypeptide with transcription factor repressor activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, N.Y., 1993). The $T_m$ is the temperature at which 50% of a given strand of a nucleic acid molecule is hybridized to its complementary strand. The following is an exemplary set of hybridization conditions and is not limiting:

| Very High Stringency (allows sequences that share at least 90% identity to hybridize) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (allows sequences that share at least 80% identity to hybridize) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (allows sequences that share at least 50% identity to hybridize) | |
|---|---|
| Hybridization: | 6x SSC at RT to 55° C. for 16-20 hours |
| Wash at least twice: | 2x-3x SSC at RT to 55° C. for 20-30 minutes each. |

In a preferred method of the invention said nucleic acid encodes a polypeptide as represented by the amino acid sequence shown in FIG. 4, or a variant amino acid sequence that has been modified by addition, deletion or substitution of at least one amino acid residue and has transcription factor repressor activity.

A variant polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan.

In addition, the invention features polypeptide sequences having at least 75% identity with the polypeptide sequence as hereindisclosed, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequence illustrated herein.

According to a further aspect of the invention there is provided a composition comprising a polypeptide as represented by the amino acid sequence shown in FIG. 4, or a variant amino acid sequence that has been modified by addition, deletion or substitution of at least one amino acid residue for the manufacture of a vaccine composition for use in the immunisation of a subject against prostate cancer.

According to a further aspect of the invention there is provided a composition comprising a nucleic acid molecule comprising a nucleic acid sequence as shown in FIG. 3, or a nucleic acid molecule that hybridises to said nucleic acid under stringent hybridisation conditions, for the manufacture of a vaccine composition for use in the immunisation of a subject against prostate cancer.

According to a further aspect of the invention there is provided an antibody specifically reactive with a polypeptide as represented by the amino acid sequence shown in FIG. 4, for the manufacture of a medicament for use in the treatment of prostate cancer.

In a preferred embodiment of the invention said antibody is a monoclonal antibody, or an active binding fragment thereof. Preferably said antibody is a humanised or chimeric antibody as herein described.

In a preferred embodiment of the invention said antibody fragment is a single chain antibody variable region fragment or a domain antibody.

According to a further aspect of the invention there is provided a method of screening a subject for prostate cancer, or a predisposition to prostate cancer, comprising the steps of:
  i) providing an isolated sample comprising prostate cells; and
  ii) detecting the expression of a nucleic acid molecule comprising a nucleic acid sequence as shown in FIG. 3, or a nucleic acid molecule that hybridises to said nucleic acid under stringent hybridisation conditions.

In a preferred method of the invention said method detects expression of mRNA. Preferably said method is a polymerase chain reaction method.

In an alternative method of the invention said method detects a polypeptide encoded by said nucleic acid molecule. Preferably said polypeptide is detected by an antibody according to the invention.

According to a further aspect of the invention there is provided non-human animal model for the analysis of the formation of prostate acini comprising the steps of:
  i) providing a preparation of prostate stem cells;
  ii) transplanting said cells into a non human animal subject; and
  iii) monitoring the differentiation and growth of the transplanted cells.

In a preferred method of the invention said non-human animal is selected from the group consisting of: mouse, rat, guinea pig, dog, non-human primate.

In a preferred method of the invention said animal is a mouse, preferably an immune compromised mouse. Preferably said mouse is a SCID mouse or an athymic nude mouse.

In a preferred method of the invention said cells are transplanted subcutaneously.

In an alternative preferred method of the invention said cells are transplanted orthotopically in or around prostate tissue.

An embodiment of the invention will now be described by example only and with reference to the following Figures:

FIG. 1: Verification of CD133 as a stem cell marker of prostatic epithelia: 1A: A paraffin section of prostatic acini labelled with the nuclear stain DAPI (Blue) and anti-CD133 directly conjugated to PE (Red). 1B: Basal cells with the phenotype $\alpha_2\beta_1^{hi}$/CD133$^+$ have a higher colony forming efficiency (CFE) than $\alpha_2\beta_1^{low}$/CD133$^-$. (CFE) was calculated as the number of colonies formed per number of selected cells × 100%. CFEs are expressed as the ratio of the control CFE. Results show means±s.e.m of four experiments. 1C. Xenografts of prostate acini formed by transplantation of $\alpha_2\beta_1^{hi}$/CD133$^+$ basal cells stained with (A) Haematoxylin and Eosin, (B) 34βE12, (C) anti-K18, (D) anti-PAP (E) Anti-androgen receptor. Bar 40 μm;

FIG. 2: Characterisation of tumour 'stem' cells from a lymph node metastasis of the prostate (LNMP). 2A. Tumour cells selected on the basis of $\alpha_2\beta_1$/CD133 differentiate in culture. 2B. Invasion assay activity of LNMP in comparison to PC3M and an immortalised prostate epithelial cell line, PNT1a;

FIG. 3 is the nucleic acid sequence of the proto-oncogene BMI; and

FIG. 4 is the amino acid sequence of the proto-oncogene BMI.

MATERIALS AND METHODS

Genotype of Isolated Tumour Stem Cells

Figure 1A:
Figure 1B:
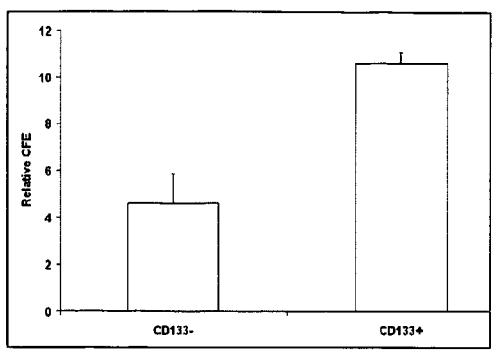
Figure 1C:
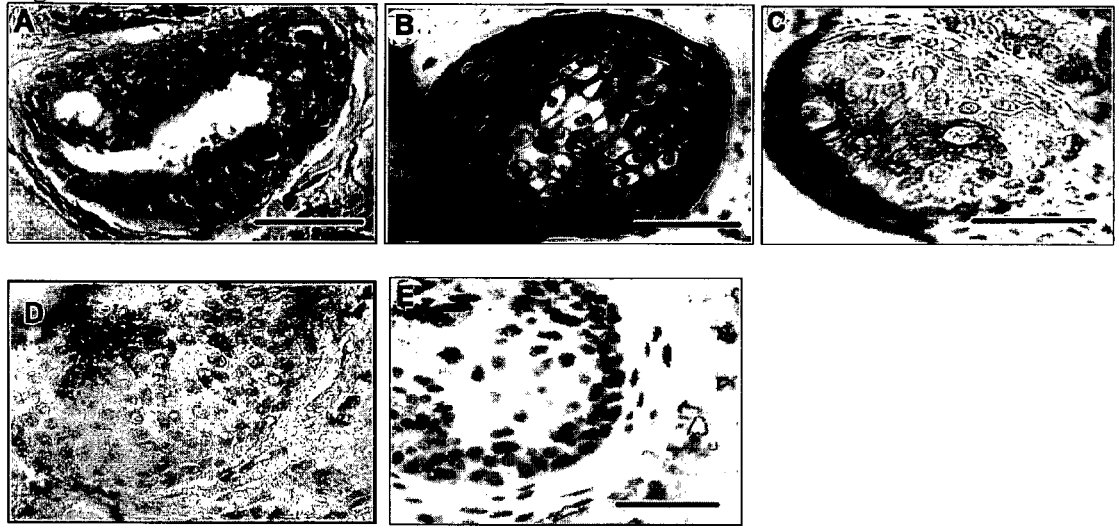
Figure 2A:
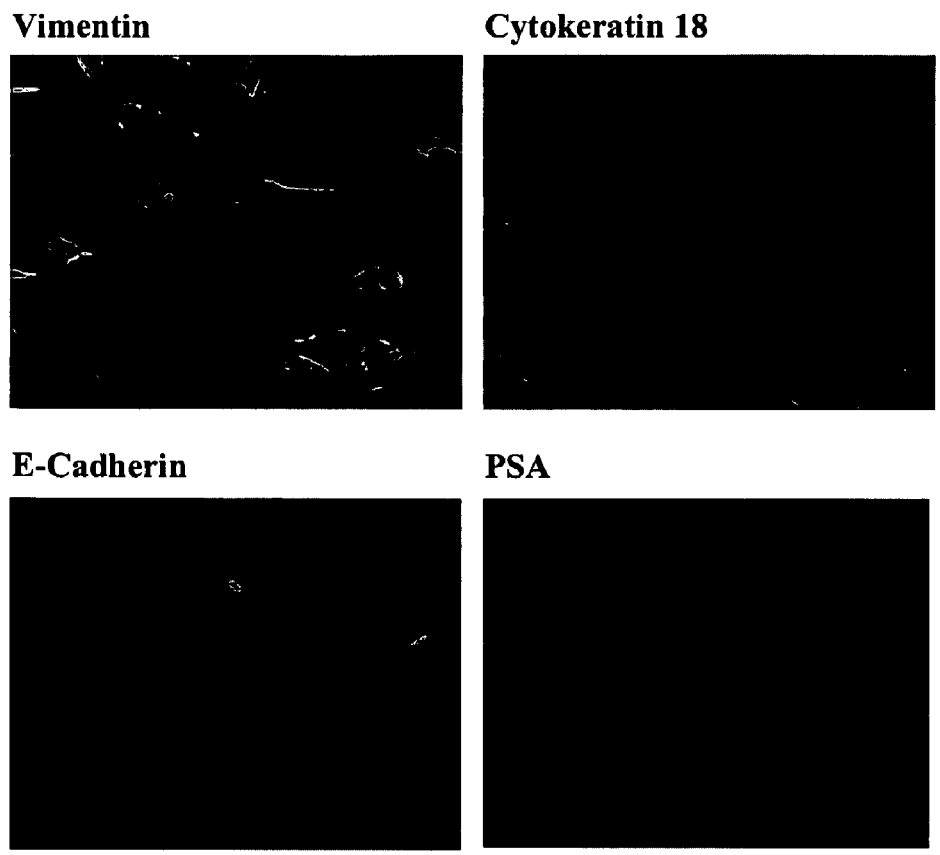
Figure 2B:
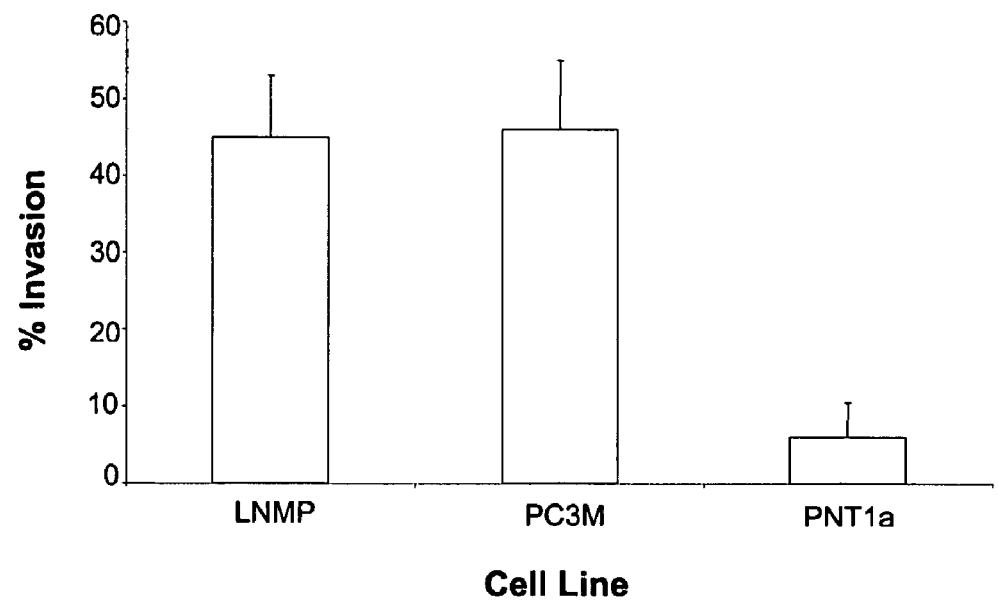

Using a combination of microsatellite markers associated with sporadic prostate cancer (8p 10q 16p, FIG. 3) we can determine whether the isolated HEA$^+$/CD44$^+$/$\alpha_2\beta_1^{hi}$/CD133$^+$ cells display loss of heterozygosity patterns characteristic of prostate tumours in comparison to blood lymphocyte DNA from the same patient. The analysis is carried out on a microsampling of cultures with 3 MM paper and fluorescently labelled PCR primers (Macintosh et al., 1998). This will enable us to discriminate between normal and cancer cells and determine whether stem cells are indeed targets for transforming events.

Proliferative, Differentiative and Malignant Potential of Putative Cancer Stem Cells Distinct populations of tumour cells are isolated and their proliferative, differentiative and malignant potential determined in vitro and in vivo. The following populations (HEA$^+$/CD44$^-$ (luminal cells), HEA$^+$/CD44$^+$ (basal cells), HEA$^+$/CD44$^+$/$\alpha_2\beta_1^{low}$/CD133$^-$ (transit cells), HEA$^+$/CD44$^+$/$\alpha_2\beta_1^{hi}$/CD133$^+$ (stem cells) are isolated and compared with the unsorted tumour population.

Colony Forming Efficiency (CFE): Anchorage Independent and Anchorage-dependent Growth The transforming potential of distinct populations (as above) of cancer cells (anchorage independence) is measured by their ability to form colonies in soft agar. Individual colonies are counted after 21 days using an inverted microscope. Comparisons are made of CFE and colony size.

Morphogenesis in Gels of Reconstituted Basement Membrane Matrix

We have determined the potential of tumour stem cells and their progenitors to undergo glandular morphogenesis in reconstituted basement membrane (e.g. Matrigel). We have demonstrated that normal basal cells can undergo glandular morphogenesis when grown in a collagen based matrix, (e.g. Matrigel) with stroma, in the presence of androgens. Spheroids are generated which are architecturally and phenotypically similar to in vivo acini and are often branched alveolar- and duct like (Lang et al., 2001). In contrast, cancer cells often form large aggregates of spindle-shaped cells with no obvious organisation. Nonetheless, the structures will often contain cells that show some degree of differentiation and can be compared to the original tumour.

Invasion Assays

The ability of these stem cells to migrate across Matrigel is determined by the modified Boyden-chamber method (Albini et al., 1987). Migration rates will be evaluated using time-lapse confocal microscopy, using cells labelled with EGFP. We have generated prostate epithelium expressing low levels of EGFP. Recombinant retrovirus based on pLNCX-EGFP(2) generated will be used to infect the cell populations and G418 resistant colonies will be used in motility assays. The low levels of GFP expression will be used to track invasion and motility in real time.

In vivo Tumourigenesis

Tumour stem cells must possess key criteria that define normal stem cells: after transplantation they must proliferate, differentiate and self-renew. To determine the ability of distinct tumour phenotypes, to colonise in vivo, grafts of stem cells, transit cells, basal cells, luminal cells and unsorted cells are introduced into the prostates of 6 to 8 week old male, immunocomprimised mice. The mice are treated hormonally at the time of grafting by subcutaneous implantation of sustained release testosterone pellets. The number of cells from each population that successfully engraft and initiate tumour proliferation is determined by varying the number of cells implanted. The self-renewal capacity of the distinct populations is determined by transplanting serially into secondary recipients.

Comparison of Gene Expression Profiles Between Cancer and Normal Stem Cells

Expression profiles are obtained from stem cells isolated from cancer containing and non-cancer tissue samples. An Affymetrix GeneChip microarray platform is used to assay the absolute gene expression levels for each sample. To accomplish this, total RNA is extracted from purified $\alpha_2\beta_1^{++}$ cells. As the cell yield is low it is necessary to use a linear amplification step to provide sufficient target for hybridisation to the arrays. The Affymetrix small sample labelling protocol has been demonstrated to work well with 100 ng (~10$^4$ cells) but can be used for as little as 1-10 ng total RNA. To date we have used this technology (Hu-U133A GeneChips) to profile amplified total RNA extracted from selected cell populations (including $\alpha_2\beta_1^{++}$) derived from our recently isolated prostate cancer lymph node metastasis cell line.

Each sample is derived from a separate individual therefore a substantial degree of variation in gene expression (both between cancer and non-cancer samples and between samples within the same class) will be due to the underling genetic heterogeneity between the individuals. As a result it is necessary to include a number of 'biological' replicates within each class of sample and we typically use 6-10 samples for each (i.e. up to 20 samples in total).

Batch comparison analysis is used to compare each cancer sample experiment to each of the non-cancer samples and subject the comparisons to three different statistical algorithms, based on the Mann-Whitney test, non-parametric Wilcoxon rank test and self-organising map cluster analysis, to detect differential expression. Furthermore, we apply cluster analysis to look for groups of genes which behave differently from the norm.

The invention claimed is:

1. A method for the selective enrichment of prostate cancer stem cells which express CD133, CD44, and high levels of $\alpha_2\beta_1$ integrin which comprises the following steps:
  i) providing a cell preparation comprising prostate cancer stem cells derived from prostate tissue;
  ii) providing cell culture conditions which allow the maintenance of said prostate cancer stem cells in culture and the binding of said prostate cancer stem cells to a collagen based matrix;
  iii) selecting said bound cells for expression of CD133 and isolating bound cells that express CD133 antigen, CD44 antigen, and $\alpha_2\beta_1$ integrin.

2. A method according to claim 1 wherein said method includes the additional steps of:
  iv) culturing prostate cancer stem cells which express CD133 antigen in culture medium comprising granulocyte macrophage colony stimulating factor (GM-CSF), stem cell factor (SCF) and leukaemia inhibitory factor (LIF); and
  v) passaging the prostate cancer stem cells in (i) in a serum free medium.

3. A method according to claim 1 wherein said selected cells express human epithelial antigen.

4. A method according to claim 1 wherein said prostate cancer stem cells are metastatic.

5. A method according to claim 1 wherein said prostate cancer stem cells are from a primary prostate tumour.

6. A method according to claim 1 wherein said collagen based matrix comprises collagen I.

7. A prostate cancer stem cell obtainable by the method of claim 1, wherein said prostate cancer stem cells have high in vitro proliferative potential, have higher colony forming efficiency than $\alpha_2\beta_1$ integrin$^{low}$ CD133$^-$ prostate cells and can form cancerous prostatic-like acini in an immune-compromised non-human animal model.

8. A prostate cancer stem cell according to claim 7 wherein said stem cell is cloned.

9. A cell culture of prostate cancer stem cells wherein said cells express CD133 antigen, CD44 antigen, and $\alpha_2\beta_1$ integrin wherein said prostate cancer stem cells have high in vitro proliferative potential, have higher colony forming efficiency than $\alpha_2\beta_1$ integrin$^{low}$ CD 133$^-$ prostate cells and can form cancerous prostatic-like acini in an immune-compromised non-human animal model.

10. A cell culture according to claim 9 wherein said prostate cancer stem cells express human epithelial antigen.

* * * * *

SEQUENCE LISTING

<160> NUMBER OF SEQ ID NOS: 2

<210> SEQ ID NO 1
<211> LENGTH: 326
<212> TYPE: PRT
<213> ORGANISM: Homo sapiens

<400> SEQUENCE: 1

Met His Arg Thr Thr Arg Ile Lys Ile Thr Glu Leu Asn Pro His Leu
1               5                   10                  15

Met Cys Val Leu Cys Gly Gly Tyr Phe Ile Asp Ala Thr Thr Ile Ile
            20                  25                  30

Glu Cys Leu His Ser Phe Cys Lys Thr Cys Ile Val Arg Tyr Leu Glu
        35                  40                  45

Thr Ser Lys Tyr Cys Pro Ile Cys Asp Val Gln Val His Lys Thr Arg
    50                  55                  60

Pro Leu Leu Asn Ile Arg Ser Asp Lys Thr Leu Gln Asp Ile Val Tyr
65                  70                  75                  80

Lys Leu Val Pro Gly Leu Phe Lys Asn Glu Met Lys Arg Arg Arg Asp
                85                  90                  95

Phe Tyr Ala Ala His Pro Ser Ala Asp Ala Ala Asn Gly Ser Asn Glu
            100                 105                 110

Asp Arg Gly Glu Val Ala Asp Glu Asp Lys Arg Ile Ile Thr Asp Asp
            115                 120                 125

Glu Ile Ile Ser Leu Ser Ile Glu Phe Phe Asp Gln Asn Arg Leu Asp
        130                 135                 140

Arg Lys Val Asn Lys Asp Lys Glu Lys Ser Lys Glu Glu Val Asn Asp
145                 150                 155                 160

Lys Arg Tyr Leu Arg Cys Pro Ala Ala Met Thr Val Met His Leu Arg
                165                 170                 175

Lys Phe Leu Arg Ser Lys Met Asp Ile Pro Asn Thr Phe Gln Ile Asp
            180                 185                 190

Val Met Tyr Glu Glu Glu Pro Leu Lys Asp Tyr Tyr Thr Leu Met Asp
            195                 200                 205

Ile Ala Tyr Ile Tyr Thr Trp Arg Arg Asn Gly Pro Leu Pro Leu Lys
        210                 215                 220

Tyr Arg Val Arg Pro Thr Cys Lys Arg Met Lys Ile Ser His Gln Arg
225                 230                 235                 240

Asp Gly Leu Thr Asn Ala Gly Glu Leu Glu Ser Asp Ser Gly Ser Asp
                245                 250                 255

Lys Ala Asn Ser Pro Ala Gly Gly Ile Pro Ser Thr Ser Ser Cys Leu
            260                 265                 270

Pro Ser Pro Ser Thr Pro Val Gln Ser Pro His Pro Gln Phe Pro His
            275                 280                 285

Ile Ser Ser Thr Met Asn Gly Thr Ser Asn Ser Pro Ser Gly Asn His
        290                 295                 300

Gln Ser Ser Phe Ala Asn Arg Pro Arg Lys Ser Ser Val Asn Gly Ser
305                 310                 315                 320

Ser Ala Thr Ser Ser Gly
                325

<210> SEQ ID NO 2
<211> LENGTH: 3251
<212> TYPE: DNA
<213> ORGANISM: Homo sapiens

<400> SEQUENCE: 2

| | | | | | |
|---|---|---|---|---|---|
| cagcaactat | gaaataatcg | tagtatgaga | ggcagagatc | ggggcgagac | aatggggatg | 60 |
| tgggcgcggg | agcccgttc | cggcttagca | gcacctccca | gccccgcaga | ataaaaccga | 120 |
| tcgcgccccc | tccgcgcgcg | ccctcccccg | agtgcggagc | gggaggaggc | ggcggcggcc | 180 |
| gaggaggagg | aggaggaggc | cccggaggag | gaggcgttgg | aggtcgaggc | ggaggcggag | 240 |
| gaggaggagg | ccgaggcgcc | ggaggaggcc | gaggcgccgg | agcaggagga | ggccggccgg | 300 |
| aggcggcatg | agacgagcgt | ggcggccgcg | gctgctcggg | gccgcgctgg | ttgcccattg | 360 |
| acagcggcgt | ctgcagctcg | cttcaagatg | gccgcttggc | tcgcattcat | tttctgctga | 420 |
| acgactttta | actttcattg | tcttttccgc | ccgcttcgat | cgcctcgcgc | cggctgctct | 480 |
| ttccgggatt | ttttatcaag | cagaaatgca | tcgaacaacg | agaatcaaga | tcactgagct | 540 |
| aaatccccac | ctgatgtgtg | tgctttgtgg | agggtacttc | attgatgcca | caaccataat | 600 |
| agaatgtcta | cattccttct | gtaaaacgtg | tattgttcgt | tacctggaga | ccagcaagta | 660 |
| ttgtcctatt | tgtgatgtcc | aagttcacaa | gaccagacca | ctactgaata | taaggtcaga | 720 |
| taaaactctc | caagatattg | tatacaaatt | agttccaggg | cttttcaaaa | atgaaatgaa | 780 |
| gagaagaagg | gattttatg | cagctcatcc | ttctgctgat | gctgccaatg | gctctaatga | 840 |
| agatagagga | gaggttgcag | atgaagataa | gagaattata | actgatgatg | agataataag | 900 |
| cttatccatt | gaattctttg | accagaacag | attggatcgg | aaagtaaaca | agacaaaga | 960 |
| gaaatctaag | gaggaggtga | atgataaaag | atacttacga | tgcccagcag | caatgactgt | 1020 |
| gatgcactta | agaaagtttc | tcagaagtaa | aatggacata | cctaatactt | tccagattga | 1080 |
| tgtcatgtat | gaggaggaac | ctttaaagga | ttattataca | ctaatggata | ttgcctacat | 1140 |
| ttatacctgg | agaaggaatg | gtccacttcc | attgaaatac | agagttcgac | ctacttgtaa | 1200 |
| aagaatgaag | atcagtcacc | agagagatgg | actgacaaat | gctggagaac | tggaaagtga | 1260 |
| ctctgggagt | gacaaggcca | acagcccagc | aggaggtatt | ccctccacct | cttcttgttt | 1320 |
| gcctagcccc | agtactccag | tgcagtctcc | tcatccacag | tttcctcaca | tttccagtac | 1380 |
| tatgaatgga | accagcaaca | gccccagcgg | taaccaccaa | tcttctttg | ccaatagacc | 1440 |
| tcgaaaatca | tcagtaaatg | ggtcatcagc | aacttcttct | ggttgatacc | tgagactgtt | 1500 |
| aaggaaaaaa | attttaaacc | cctgatttat | atagatatct | tcatgccatt | acagctttct | 1560 |
| agatgctaat | acatgtgact | atcgtccaat | ttgctttctt | ttgtagtgac | attaaatttg | 1620 |
| gctataaaag | atggactaca | tgtgatactc | ctatggacgt | taattgaaaa | gaaagattgt | 1680 |
| tgttataaag | aattggtttc | ttggaaagca | ggcaagactt | tttctctgtg | ttaggaaaga | 1740 |
| tgggaaatgg | tttctgtaac | cattgtttgg | atttggaagt | actctgcagt | ggacataagc | 1800 |
| attgggccat | agtttgttaa | tctcaactaa | cgcctacatt | acattctcct | tgatcgttct | 1860 |
| tgttattacg | ctgttttgtg | aacctgtaga | aaacaagtgc | tttttatctt | gaaattcaac | 1920 |
| caacggaaag | aatatgcata | gaataatgca | ttctatgtag | ccatgtcact | gtgaataacg | 1980 |
| atttcttgca | tatttagcca | ttttgattcc | tgtttgattt | atacttctct | gttgctacgc | 2040 |
| aaaaccgatc | aaagaaaagt | gaacttcagt | tttacaatct | gtatgcctaa | aagcgggtac | 2100 |
| taccgtttat | tttactgact | tgtttaaatg | attcgctttt | gtaagaatca | gatggcatta | 2160 |

-continued

```
tgcttgttgt acaatgccat attggtatat gacataacag gaaacagtat tgtatgatat    2220
atttataaat gctataaaga aatattgtgt ttcatgcatt cagaaatgat tgttaaaatt    2280
ctcccaactg gttcgacctt tgcagatacc cataacctat gttgagcctt gcttaccagc    2340
aaagaatatt tttaatgtgg atatctaatt ctaaagtctg ttccattaga agcaattggc    2400
acatctttct atactttata tacttttctc cagtaataca tgtttacttt aaaaattgtt    2460
gcagtgaaga aaaacccttta actgagaaat atggaaaccg tcttaattt ccattggcta    2520 tgatggaatt aatattgtat tttaaaatg catattgatc actataattc taaaacaatt    2580
ttttaaataa accagcaggt tgctaaaaga aggcatttta tctaaagtta ttttaatagg    2640
tggtatagca gtaattttaa atttaagagt tgcttttaca gttaacaatg gaatatgcct    2700
tctctgctat gtctgaaaat agaagctatt tattatgagc ttctacaggt attttttaaat    2760 agagcaagca tgttgaattt aaaatatgaa taaccccacc caacaattt cagtttattt    2820 tttgctttgg tcgaacttgg tgtgtgttca tcacccatca gttatttgtg agggtgttta    2880
ttctatatga atattgtttc atgtttgtat gggaaaattg tagctaaaca tttcattgtc    2940
cccagtctgc aaaagaagca caattctatt gctttgtctt gcttatagtc attaaatcat    3000 tactttaca tatattgctg ttacttctgc tttctttaaa aatatagtaa aggatgtttt    3060
atgaagtcac aagatacata tattttttatt ttgacctaaa tttgtacagt cccattgtaa    3120
gtgttgtttc taattataga tgtaaaatga aatttcattt gtaattggaa aaaatccaat    3180
aaaaaggata ttcatttaga aaaaaaaaaa aaaaaaaaaa aaaaaaaaaa aaaaaaaaaa    3240
aaaaaaaaaa a                                                         3251
```